US007575561B2

(12) United States Patent
Smith et al.

(10) Patent No.: US 7,575,561 B2
(45) Date of Patent: Aug. 18, 2009

(54) ABOVE KNEE SHRINKER

(75) Inventors: Mark W. L. Smith, DeSoto, KS (US);
Jeffrey C. Dalbey, Leawood, KS (US);
Frederick B. Lanier, Jr., Olathe, KS (US)

(73) Assignee: Knit Rite, Inc., Kansas City, KS (US)

( * ) Notice: Subject to any disclaimer, the term of this patent is extended or adjusted under 35 U.S.C. 154(b) by 732 days.

(21) Appl. No.: 10/707,930

(22) Filed: Jan. 26, 2004

(65) Prior Publication Data
US 2005/0165341 A1    Jul. 28, 2005

(51) Int. Cl.
*A61F 13/00*    (2006.01)
(52) U.S. Cl. .............................. 602/60; 602/61; 602/62
(58) Field of Classification Search ............ 602/60–62, 602/26; 128/882
See application file for complete search history.

(56) References Cited

U.S. PATENT DOCUMENTS

| 1,172,927 | A | * | 2/1916 | Bloch | 2/68 |
| 2,688,136 | A | * | 9/1954 | Freedman | 2/105 |
| 3,032,035 | A | * | 5/1962 | Dempsey | 602/61 |
| 3,138,156 | A | * | 6/1964 | Crowell et al. | 602/61 |
| 3,237,210 | A | * | 3/1966 | Graber | 2/209.11 |
| 3,285,307 | A | * | 11/1966 | Dormaier | 383/4 |
| 3,449,766 | A | * | 6/1969 | Friedman et al. | 2/209.12 |
| 4,495,660 | A | * | 1/1985 | Hayden | 2/91 |
| 4,644,946 | A | * | 2/1987 | Cremona-Bonato | 602/61 |
| 4,840,635 | A | * | 6/1989 | Smith et al. | 623/36 |
| 4,937,885 | A | * | 7/1990 | Gregg | 2/209.11 |
| 5,063,919 | A | * | 11/1991 | Silverberg | 602/3 |
| 5,376,130 | A | * | 12/1994 | Courtney | 623/33 |
| 5,417,091 | A | * | 5/1995 | Moser | 66/178 R |
| 5,768,712 | A | * | 6/1998 | Barlow | 2/400 |
| 5,873,903 | A | * | 2/1999 | Garcia | 607/108 |
| 5,916,190 | A | * | 6/1999 | Davis, Jr. | 602/41 |
| 6,047,403 | A | * | 4/2000 | Juozaitis | 2/61 |
| 6,158,253 | A | * | 12/2000 | Svoboda et al. | 66/178 R |
| 6,440,172 | B1 | * | 8/2002 | Davant et al. | 623/36 |
| 6,978,643 | B2 | * | 12/2005 | Akers et al. | 66/170 |

OTHER PUBLICATIONS

Yeongchi Wu, *Postoperative and Preprosthetic Management for Lower Extremity Amputations in Haimovici's Vascular Surgery*, title page and Chapter 107, pp. 1348-1354, ( Henry Haimovici et al., 4th ed., published prior to Jan. 26, 2003).
Yeongchi Wu, *Managing Residual Limbs with Elastic Stockinette*, Center for International Rehabilitation, Technical Brief (No. 1, Dec. 1999).
Knit-Rite, Inc., Knit-Rite Catalog #14 60-64 (2001).

* cited by examiner

*Primary Examiner*—Michael A. Brown
(74) *Attorney, Agent, or Firm*—Hovey Williams LLP

(57) ABSTRACT

An above knee shrinker includes a tubular fabric receptacle that encloses and applies therapeutic compression to the residual limb of a human trans-femoral lower-leg amputee. The shrinker includes a constricting element, and a moveably coupled waist belt. The receptacle is configured to present an overhanging portion that extends below the distal end of the residual limb and is able to be doubled-over at least a portion of the residual limb to apply additional compression thereto. The receptacle is configured to provide an improved U-shaped perineal opening. The receptacle is formed of a latex-free core spun yarn and spandex material that is comfortably stretchable in at least first and second substantially transverse directions. The waist belt presents an adjustable self-fastening mechanism, and the constricting element presents a sliding-ring that receives the overhanging portion and constricts the receptacle adjacent the distal end of the residual limb.

19 Claims, 2 Drawing Sheets

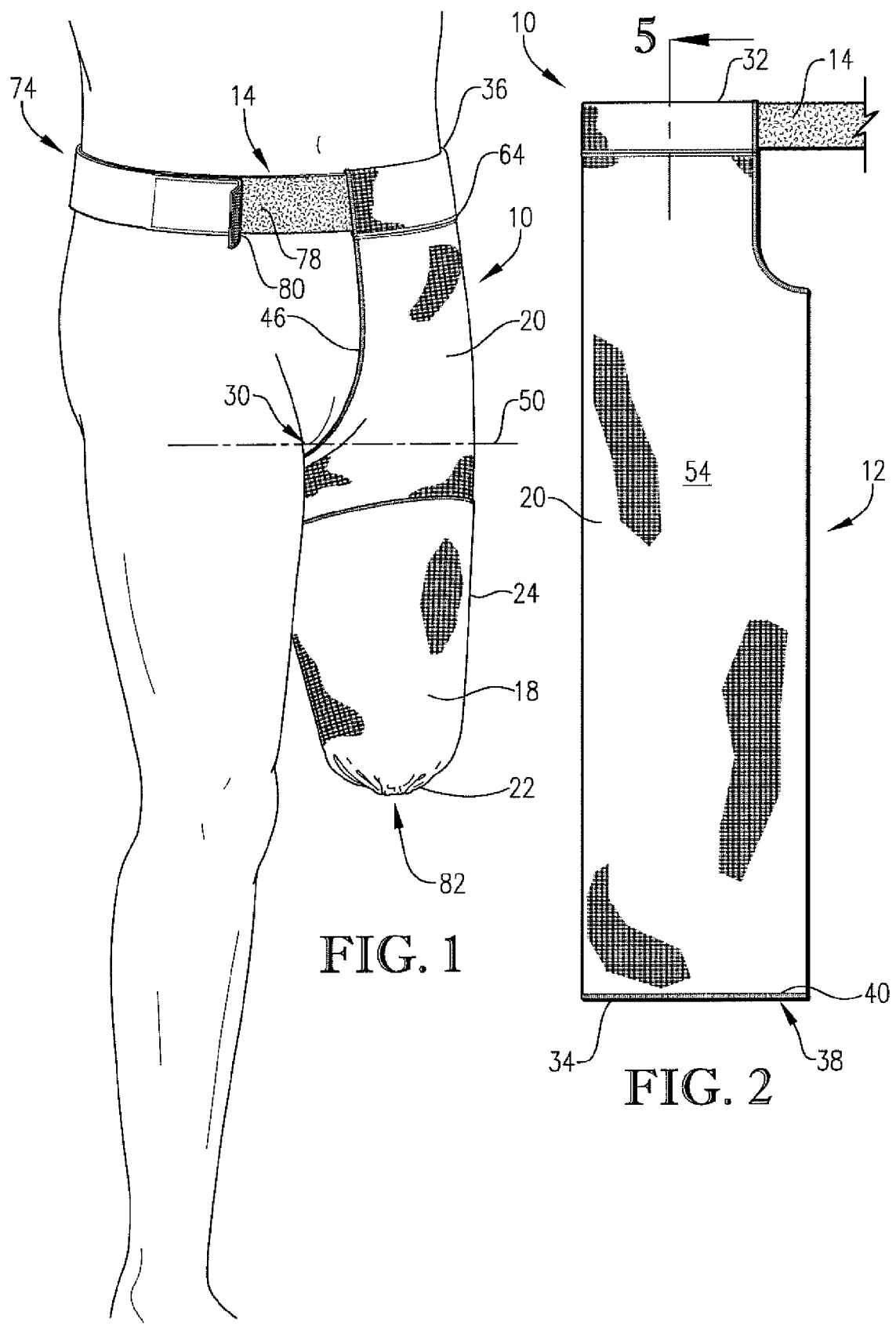

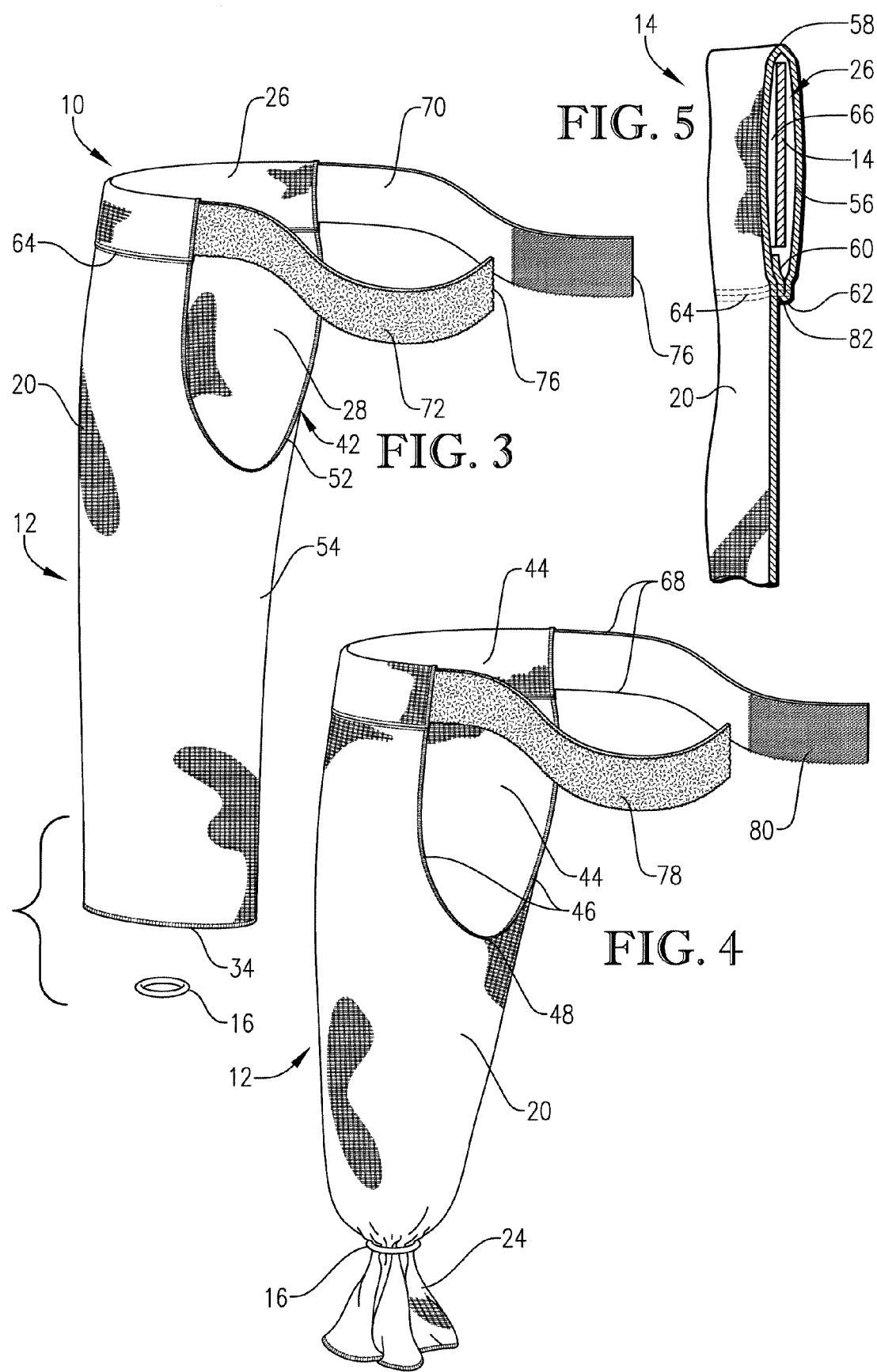

ABOVE KNEE SHRINKER

BACKGROUND OF INVENTION

1. Field of the Invention

The present invention relates generally to manufactured textile products for lower-leg amputees. More specifically, the present invention concerns an above knee shrinker designed to comfortably apply therapeutic compression to the residual limb or stump of a lower-leg amputee.

2. Discussion of Prior Art

Compressive above knee shrinkers have been developed to post-operatively provide therapeutic compression to the residual limb of lower-leg or transfemoral amputee patients. The therapeutic compressive force applied by these shrinkers have been used to control and maintain stable soft tissue fluid volume, to reduce operative edema in the residual limb, and if worn nightly, to facilitate the fitting of a prosthesis the next morning. Conventional above knee shrinkers have incorporated waist belts and typically present tapered receptacles that extend to the belts, in an effort to vertically secure the shrinkers and, thereby, alleviate unwanted slippage and dislodgment.

These shrinkers, however, present various problems and disadvantages. For example, the addition of belts has sacrificed comfort for stability by intruding the receptacle upon the amputee's perineal region. Yet another problem is presented by the lack of lengthwise adjustability in conventional receptacles, which necessitates more shrinker sizes, and causes discomfort during donning.

Thus, a need exists for a vertically secure shrinker that provides additional comfort and the desired compression to the residual limb of the wearer.

SUMMARY OF INVENTION

Responsive to these and other problems caused by conventional shrinkers, the present invention concerns an improved above knee shrinker for applying therapeutic compression to the residual limb of a lower-leg amputee. The invention provided hereof, among other things, is useful for providing more comfort to the wearer during use and donning, easier to don than conventional above knee shrinkers, and particularly effective in providing the desired compression.

A first aspect of the present invention concerns an above knee shrinker comprising a waist belt dimensioned for snugly receiving the waist of the wearer, and a tubular fabric receptacle dimensioned and configured to be worn on and apply a compressive force to the residual limb. The receptacle presents top and bottom ends, and is open adjacent each of the ends so that the residual limb can be inserted into the receptacle adjacent the top end. The receptacle is coupled to the waist belt adjacent the top end so that snug securement of the waist belt about the wearer's waist restricts vertical displacement of the receptacle along the residual limb. The receptacle is dimensioned so as to be longer than the residual limb, thereby permitting the receptacle to be doubled over the residual limb. The receptacle also includes a U-shaped edge projecting from the top end that presents a U-shaped perineal opening adjacent the torso end of the residual limb. Finally, the U-shaped edge includes a pair of spaced apart upright sections extending from the top end and a bottom section that is spaced from the top end and interconnects the upright sections.

A second aspect of the present invention concerns an above knee shrinker comprising a waist belt dimensioned for snugly receiving the waist of the wearer, and a tubular fabric receptacle dimensioned and configured to be worn on and apply a compressive force to the residual limb. The receptacle presents top and bottom ends, and is open adjacent each of the ends so that the residual limb can be inserted into the receptacle adjacent the top end. The receptacle is coupled to the waist belt adjacent the top end so that snug securement of the waist belt about the wearer's waist restricts vertical displacement of the receptacle along the residual limb. The receptacle is dimensioned so as to be longer than the residual limb, thereby permitting the receptacle to be doubled over the residual limb. Finally, the receptacle is knitted at least principally of core-spun yarn and includes a plurality of laid in elastic threads.

In a preferred embodiment of the above knee shrinker, the receptacle further includes a channel located adjacent the top end, a waist belt having two separate ends and a self-fastening adjustable mechanism, and a constrictive element operable to constrict the receptacle adjacent the distal end of the residual limb.

Other aspects and advantages of the present invention will be apparent from the following detailed description of the preferred embodiment and the accompanying drawing figures.

BRIEF DESCRIPTION OF DRAWINGS

A preferred embodiment of the invention is described in detail below with reference to the attached drawing figures, wherein:

FIG. 1 is a perspective view of the above knee shrinker constructed in accordance with the present invention, particularly showing the shrinker in a doubled-over-condition for more, distal pressure and being donned by a human lower-leg amputee;

FIG. 2 is a fragmentary elevation view of the shrinker in an unworn condition;

FIG. 3 is an exploded perspective view of the shrinker, particularly illustrating the sliding-ring constricting element and the self-fastening mechanism at the belt ends;

FIG. 4 is a perspective view of the shrinker, particularly illustrating the sliding-ring constricting element received over the receptacle;

FIG. 5 is an enlarged, fragmentary perspective-cross sectional view of the top end of the receptacle, particularly illustrating the belt receiving channel of the receptacle.

DETAILED DESCRIPTION

The above knee shrinker 10, selected for illustration in FIGS. 1-5, generally comprises a multi-directional stretch tubular fabric receptacle 12, a waist belt 14, and a constricting element 16. The shrinker 10 is operable to encircle and enclose the residual limb 18 of a lower-leg human amputee in a vertically secure position, and is suitably formed so as to apply a therapeutic compressive force to the residual limb 18. It is appreciated by those skilled in the art that the application of compressive force to the residual limb 18 reduces the risk of edema.

As best shown in FIG. 1, the receptacle 12 forms the primary component of the shrinker 10 and receives the residual limb 18. The receptacle 12 is dimensioned to conform to the contours of the residual limb 18 and provide an overhanging portion 24 that extends beyond the distal end 22 of the residual limb 18. The receptacle 12 presents a U-shaped perineal opening 28 to prevent uneven contact between the receptacle 12 and the amputee's perineal region 30. Finally, the receptacle 12 also includes a belt-receiving channel 26 adjacent the top end 36.

Turning first to the construction of the shrinker 10, the receptacle 12 is weft knitted in one entire piece on a circular rib-knit machine (not shown), although other suitable knitting or fabricating techniques may be used. One such machine is available as Model No. R1428 from Tompkins Brothers Company, Inc. The preferred receptacle 12 is knitted in connected loops of substantially uniform pattern and number per square inch throughout the receptacle 12. More preferably, the receptacle 12 is formed in a one-by-one rib stitch knitting pattern.

To provide a more uniform compressive force, the receptacle 12 is at least predominately formed of multidirectional stretchable material, which shall be interpreted to mean herein material that is substantially able to be equally stretched in a first direction and a second direction substantially transverse to the first direction. More preferably, under normally anticipated loads, the material is at least capable of stretching 50% in a first direction, such as the typical weft direction, and 45% in a second direction perpendicular to the first direction, such as the typical warp direction. Most preferably, the material is capable of stretching at least 70% in the first direction, and 65% in the second direction under the same conditions. It is appreciated that the multi-directional stretchable material is concurrently stretchable in both the first and second directions, so as to provide stretchability in all directions.

In the preferred embodiment, the multi-directional stretchable material comprises core-spun yarn and elastic laid in at least every fourth course of knitted yarn. The core-spun yarn includes a spandex core and a latex-free fiber sheathing. The sheathing includes polyester fiber or a polyester/x-static® blend. The spandex core primarily provides the stretchability of the shrinker 10 and helps to generate the compressive force. An acceptable brand of spandex to be used for the core is forty denier LYCRA brand spandex available from E.I. DuPont Nemours & Co., Inc., of Wilmington, Del. Finally, the elastic continuously laid in every fourth course is preferably a covered spandex yarn. One suitable brand of elastic yarn, designated as "CM8414.T9.087C" from UNIFI, Inc., of Charlotte, N.C., consists of a double-covered filament polyester around a Dorlastan spandex.

The material components are proportionally provided as needed to effect the aforementioned multi-directional stretchability of the receptacle 12. More preferably, the core-spun yarn comprises about 95% fiber sheathing, and 5% spandex. It is within the purview of this invention, however, to utilize other types of yarn suitable for providing the desired multi-directional stretch functionality, in the construction of the receptacle 12. Finally, the receptacle 12 preferably utilizes a dyeable yarn material that is capable of piece dyed, as commonly known in the art. The blend of core-spun yarn and elastic thread described above presents such a dyeable fabric material.

It is appreciated that the preferred pattern and material composition of the receptacle 12 result in generally uniform compression against the residual limb 18 over a wide range of stretch. It is also appreciated, however, that the receptacle 12 can be formed in varying patterns and densities, so as to present areas of different compressive strengths under equal stretches. For example, the over-hanging portion 24 could present a different knit pattern or density that applies a different compressive force to the residual limb 18 than does the main portion 20 of the receptacle 12.

As shown in FIGS. 1-4, the open edges of the receptacle 12, including the outermost courses of yarn are reinforced with cover stitching 40 knitted in a manner commonly known to those skilled in the art. Generally coextensive with the width and length of the first course, the reinforcing cover stitching 40 is provided at or near the edges to deter fraying at these stress points. The stitching 40 is tight, even and well-set into the material. The stitching 40 is constructed in a commonly known pattern or configuration and with similarly stretchable material operable to effect the intended function of the shrinker 10. One such suitable stitching material is designated as "Stretch Nylon" and manufactured by Sapona Manufacturing Co., Inc. of Charlotte, N.C.

Turning to the configuration of the shrinker 10, the receptacle 12 presents three distinguishable sections: a tubular body 54 consisting of main and overhanging portions 20 and 24, the U-shaped perineal opening 28, and the belt receiving channel 26. The body 54 and belt receiving channel 26 one preferably integrally knitted as one continuous unit. Alternatively, component parts of the shrinker 10 may be separately constructed and later compiled. It is appreciated, however, that continuous construction of the receptacle 12 provides a more comfortable seamless structure and also reduces post-production labor costs associated with sewing the parts together.

As best shown in FIG. 3, the tubular body 54 presents an open bottom end 38 and an open top end 36 defined by a bottom edge 34 and a top edge 32 respectively. In the preferred embodiment, the ends 36 and 38 of the body are generally equal in diameter, resulting in a non-tapered tubular body having parallel sides, as shown in FIG. 2. It is essential that the diameter of the body 54 be measurably smaller than the average residual limb diameter so as to be stretched when donned. It is believed that the multi-directional stretchability provided by the material enables the intended conformation of the receptacle 12 to the contours of the residual limb, despite the non-tapered configuration. It is also appreciated by those skilled in the art that the non-tapered configuration reduces manufacturing costs associated with tapered conventional shrinkers.

The receptacle 12 is preferably of sufficient length to enable the overhanging portion 24 to be stretched and doubled-over a predominate portion of the residual limb. More preferably, the portion 24 presents a length not less than one-half of the lengthwise dimension of the residual limb. Where desired, excess length can be removed by laterally cutting the overhanging portion 24 to present a new lengthwise dimension. However, when cutting is desired it is preferred that the overhanging portion 24 be formed of an anti-fraying material.

Preferably, each layer of the shrinker 10 compresses the residual limb 18 with a force that is approximately equal to one-half of the compressive force exhorted by a single-layer of a conventional intermediate to heavy strength above knee shrinker. For example, each layer of the shrinker 10 in the doubled-over condition can exhort a compressive strength of 25 to 30 mmHg at 50% stretch, so as to cooperatively provide the compression of an intermediate strength shrinker having a 50 to 60 mmHg compressive strength at 50% stretch. Thus, it is appreciated that the shrinker 10 presents an equivalent intermediate strength shrinker in the doubled-over condition.

Adjacent the open top end 36, the tubular body of the receptacle 12 presents a U-shaped perineal opening 28. As shown in FIGS. 1-4, the U-shaped perineal opening 28 is defined by a U-shaped edge 42 that intercepts the open top edge 32 to cooperatively define a residual limb opening 44 consisting of the U-shaped opening 28 and the open top end

36. The U-shaped edge 42 includes a pair of spaced apart generally parallel edges 46 extending from the top edge 32 and an arcuate shaped edge 48 that interconnects the parallel edges 46 at their lower ends and is spaced from the top end 36. The parallel edges 46 are oriented in the general upright or warp direction, as best shown in FIG. 2, and the arcuate shaped edge 48 presents a vertex defined by the lowermost point on the U-shaped edge.

The U-shaped edge is configured to facilitate the comfortable wear of the tubular above knee shrinker 10 by preventing uneven contact between the shrinker 10 and the general perineal region 30 of the amputee. To this effect, the parallel edges 46 are spaced apart on the non-stretched tubular circumference of the receptacle 12 a sufficient distance. More preferably, the parallel edges 46 are spaced so as to present an open quadrant centered adjacent the perineal region 30 of the amputee. Most preferably the parallel edges 46 are spaced so as to present an open circular arc of 120° on the non-stretched tubular circumference of the receptacle 12 centered adjacent the perineal region 30 of the amputee. The parallel edges 46 also present individual lengths necessary to begin the arcuate shaped edge 48 at a nonencroaching location spaced from the top edge 32. More preferably, the parallel edges 46 present individual lengths not less than the diameter of the non-stretched tubular receptacle 12. Most preferably, the parallel edges present individual lengths not less than one and a half times the diameter of the non-stretched tubular receptacle. Finally, the arcuate shaped edge is preferably dimensioned so as to further provide clearance between the shrinker 10 and the perineal region 30 of the amputee. More preferably, the arc length of the arcuate shaped edge 48 is equal to or greater than the diameter of the receptacle 12 and the vertex is spaced at least two centimeters (cm) from a horizontal tangent 50 that includes the lowermost point of the region, as shown in FIG. 1. Thus, the entire U-shaped opening 28 is directly proportional to the diameter of the tubular receptacle 12, whereas the diameter is preferably varied according to the dimensions of an average human in a particular group size, i.e. small, medium, large, extra large, etc.

Similar to the open top and bottom edges 32 and 34, the U-shaped edge 42 is provided with cover stitching 52 co-extensively applied thereto and in a manner commonly known in the art. The cover stitching 52 is formed of similarly stretchable material, and sufficiently sized to prevent normal wear and tear along the U-shaped edge 42.

The shrinker configuration also includes the belt-receiving channel 26 adjacent the open top end 36 of the receptacle 12. The channel 26, shown in detail in FIG. 5, is formed by folding the body upon itself in the radially inward direction to present a second inner layer 56 of tubular material having a bottom inner edge, a first fold line 58 presenting the top edge 32 of the receptacle 12, and a height preferably equal to at least one and a half times the belt height. The bottom inner edge is then folded back up in between the second inner layer 56 and the receptacle 12 to present a second fold line 62, and a third intermediate layer 60 preferably having a height not greater than half the belt height. The second fold line 62 forms the bottom edge of the channel. A continuous cross stitch 64 that extends the entire length of the channel is provided at or near the second fold line 62 to permanently secure the three layers in the above configuration. Other means of attaching the three layers of the channel, such as a plurality of shorter discontinuous stitches, adhesives, and/or fasteners may also be utilized. Together the receptacle 12, second inner layer 56, and intermediate layer 60 are sufficiently dimensioned to form a channel opening 66 that is operable to receive the corresponding waist belt 14 of the shrinker 10.

As best shown in FIG. 1, the waist belt 14 is provided to prevent migration of the receptacle 12 down the residual limb 18 when the shrinker 10 is donned by the amputee. The belt 14 comprises a band of flexible material having upper and lower edges 68, an inner surface 70, and an outer surface 72. The belt 14 presents a belt height and a total unfastened length sufficient to comfortably encircle the amputee's waist 74. More preferably, the belt 14 presents a height of about five cm and a selectively variable length at least equal to one and a quarter times the circumference of the amputee's waist 74.

The belt 14 is preferably formed of a soft fabric, such as an elasticized loop material, that is elastically stretchable in at least the weft direction. As shown in FIGS. 3-4, the belt 14 is discontinuous and, therefore, presents two end edges 76 that enable the belt 14 to be passed through the channel opening 66 of the receptacle 12. It is appreciated that the slide-ability of the belt 14 enables the belt opening to be repositioned so as to enable the shrinker 10 to be used as either a left or right shrinker.

Similarly to the receptacle edges, the belt's upper, lower and end edges 68 and 76 are preferably provided with reinforcing stitching sufficiently sized and configured to prevent normal wear and tear along the entire belt edge.

The belt 14 also includes an adjustable self-fastening mechanism for securing the belt 14 around the waist 74 of the amputee. The preferred mechanism shown in FIGS. 3 and 4 is attached to the belt adjacent the belt ends, and includes a loop strip 78 and at least one hook strip 80. The strips 78,80 are operable to interconnect along a contact plane when brought to bear against one another. The loop strip 78 is sufficiently greater in length than the hook strip 80 to present varying belt circumferential lengths depending on where the hook strip 80 is placed thereupon. More preferably, the loop strip 78 co-extensively covers one of the surfaces 70,72 of the belt 14, and the hook strip 80 is placed on the opposite surface adjacent one of the belt ends. The hook strip 80 has sufficient surface area and hook density to present a total grab strength along the contact plane that is greater than the shearing force exhorted by the elasticity of the belt 14 or friction encountered during normal use. For example, on a belt having a 5 cm width, each of the hook strips 80 preferably presents a density of at least twenty-five hooks/cm$^2$ and is at least nine cm long to present a surface area of at least forty-five cm$^2$. One such hook and loop fastener is commercially available under the designation "VELCRO." However, other conventional means of adjustably fastening the belt ends around the amputee's waist 74, including buckles, snaps, pins, and clips may be utilized. Alternatively, a continuous belt could be integrally formed with or later fixed to the receptacle 12 to effect the intended purpose. In this arrangement, a fastening-mechanism is not provided since the elastic compressive strength of the belt is sufficient to vertically secure the belt.

As previously indicated, the illustrated shrinker configuration lastly includes a constricting element operable to constrict the receptacle 12 at a desired location. As shown in FIG. 1, the constricting element is adapted to engage and bear against the distal end 22 of the residual limb 18 when the shrinker 10 is donned in the final doubled-over condition. As best shown in FIGS. 3 and 4, the constricting element is preferably a circular sliding-ring 16 having a sufficient diameter for allowing the overhanging portion 24 of the receptacle 12 to pass therethrough. When the shrinker 10 is donned, the sliding-ring 16 is positioned on the receptacle 12 to define the main portion 20 and the overhanging portion 24 which is doubled-over to cover the adjacent part of the main portion 20. The portions 20,24 cooperatively present a distal constricted margin 82 of the receptacle 12 that extends along the sliding-ring 16 and is positioned adjacent the distal end 22 (see FIG. 1). The ring preferably presents an average diameter that is smaller than the smallest diameter adjacent the distal end of the residual limb 18, which prevents the ring and, therefore, the shrinker 10 from riding up the residual limb 18 when the shrinker 10 is donned.

The sliding-ring 16 preferably presents a homogenous unitary body formed of a suitable chemically non-reactive and stable material having sufficient strength for the intended purpose, such as plastic, wood, or certain epoxy compounds. More preferably, the ring comprises a rigid but non-brittle plastic donut having a smooth elliptical or circular cross-sectional shape to present no sharp edges, as shown in FIG. 3. However, it is within the purview of the invention to incorporate other suitable constricting element configurations.

The operation of the above knee shrinker 10 can best be seen from the three conditions exhibited by FIGS. 2, 4, and 1 consecutively. As best shown in FIG. 2, the shrinker 10 is first oriented in a vertical position with the top end 36 and waist belt 14 on top. The end edges 76 of the discontinuous waist belt 14 are unfastened to allow the entry of the amputee's waist 74. The amputee then places his or her residual limb 18 into the shrinker 10 through the residual limb opening 44 after orienting the shrinker 10 so that the U-shaped perineal opening 28 is received radially inward and adjacent his or her perineal region 30. After pulling the receptacle 12 to the desired vertical position, the belt 14 is fastened to appropriately compress the amputee's waist 74.

As shown in FIG. 4, the overhanging portion 24 is passed through the sliding-ring 16 a sufficient distance to prevent the unwanted dislodgment of the ring while the residual limb 18 is inserted into the receptacle 12. Although the ring 16 eliminates the need for twisting of the body 54, the overhanging portion 24 may first be twisted before being passed through the ring to further prevent dislodgment. In either case, the overhanging portion 24 of the receptacle 12 is doubled-over and stretched upward until the sliding-ring 16 reaches the distal end 22 of the residual limb 18 as shown in FIG. 1. The doubled-over overhanging portion 24 can be further stretched to provide compression over an additional area of the residual limb 18 at the amputee's discretion. If the overhanging portion 24 is of sufficient length, it is within the purview of this invention to again double-over the doubled-over portion to present more than two layers of compressive strength when required.

Those ordinarily skilled in the art will appreciate that such use of the shrinker 10 reduces discomfort and/or injury during donning. That is, the shrinker 10 is easier to don than conventional shrinkers providing the same degree of compression. This is principally attributable to the fact that, with the illustrated shrinker 10, the user can initially pull on only the main portion 20, which is less tight than the conventional shrinker and then reflect the overhanging portion 24 over the residual limb as described. In some cases, the portion 24 will not be pulled up on the residual limb as far as the main portion 20 so as to provide gradient compression.

It is also within the purview of the invention to not double over the over-hanging portion 24 of the shrinker 10 if additional compression is not desired. In this instance, any excess material of the portion 24 may be removed.

Alternatively, the shrinker 10 can be donned without the use of the sliding-ring 16. In this embodiment, the overhanging portion 24 is simply twisted adjacent the distal end 22 of the residual limb 18, after the shrinker 10 is vertically secured to the amputee and prior to doubling-over the overhanging portion 24.

The preferred forms of the invention described above are to be used as illustration only, and should not be utilized in a limiting sense in interpreting the scope of the present invention. Obvious modifications to the exemplary embodiments, as set forth herein, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

The invention claimed is:

1. An above knee shrinker for applying therapeutic compression to a wearer's leg residual limb, said above knee shrinker comprising:

a waist belt dimensioned for snugly receiving the waist of the wearer;

a tubular fabric receptacle dimensioned and configured to be worn on the residual limb and apply a compressive force to the residual limb when the shrinker is donned, said receptacle presenting top and bottom ends and being open adjacent each of the ends so that the residual limb can be inserted into the receptacle adjacent the top end, said receptacle being coupled to the waist belt adjacent the top end so that snug securement of the waist belt about the wearer's waist restricts vertical displacement of the receptacle along the residual limb when the shrinker is donned, said receptacle being dimensioned so as to be longer than the residual limb, said receptacle including a U-shaped edge projecting from the top end so as to present a U-shaped perineal opening, with said perineal opening being adjacent the torso end of the residual limb when the shrinker is donned, said U-shaped edge including a pair of spaced apart upright sections extending from the top end and a bottom section that is spaced from the top end and interconnects the upright sections;

said receptacle being knitted at least principally of core-spun yarn, said receptacle including a plurality of laid in elastic threads; and a constricting element operable to constrict the receptacle so as to facilitate doubling over of the receptacle, said constricting element receiving the receptacle to define a main tubular portion and a doubled over tubular portion that cooperatively present a distal constricted margin of the receptacle generally at the constricting element, with the constricting element engaging a distal end of the residual limb when the shrinker is donned to restrict migration of the receptacle up the residual limb, said doubled over tubular portion covering at least part of the main tubular portion, wherein the bottom end of the receptacle is spaced between the top end of the receptacle and the distal constricted margin, said constricting element being vertically moveable along the receptacle to adjust a length of the doubled over portion of the receptacle.

2. The above knee shrinker as claimed in claim 1, said top end and said U-shaped edge cooperatively defining a residual limb opening through which the residual limb is inserted when the shrinker is donned, said perineal opening forming part of the residual limb opening.

3. The above knee shrinker as claimed in claim 1, each of said upright sections being generally linear and when the shrinker is donned.

4. The above knee shrinker as claimed in claim 3, said bottom section having an arcuate shape.

5. The above knee shrinker as claimed in claim 1,
said constricting element operable to constrict the receptacle generally adjacent to the distal end of the residual limb when the shrinker is donned.

6. The above knee shrinker as claimed in claim 5,
said constricting element including a ring received over the receptacle,
said ring being adapted to engage and bear against the distal end of the residual limb when the shrinker is donned.

7. The above knee shrinker as claimed in claim 1,
said receptacle being predominantly formed of multi-directional stretchable material.

8. The above knee shrinker as claimed in claim 1,
said core-spun yarn comprising a spandex core and a fiber sheathing.

9. The above knee shrinker as claimed in claim 8,
said core-spun yarn comprising about 95% fiber sheathing and 5% spandex.

10. The above knee shrinker as claimed in claim 1,
each of said threads being laid into at least every fourth course of the knitted corespun yarn.

11. The above knee shrinker as claimed in claim 10,
each of said elastic including spandex.

12. The above knee shrinker as claimed in claim 1,
said receptacle including a belt-receiving channel adjacent the top end,
said channel being dimensioned to removably receive the waist belt,
said waist belt presenting two separate belt ends, and including an adjustable self-fastening mechanism.

13. The above knee shrinker as claimed in claim 12,
said adjustable self-fastening mechanism comprising strips of hook and loop fastening material adjacent the belt ends.

14. The above knee shrinker as claimed in claim 1,
said receptacle being formed by a continuous circular rib-knit construction so as to be seamless.

15. The above knee shrinker as claimed in claim 1,
said receptacle being stitched of a one-by-one rib stitch knitting pattern.

16. The above knee shrinker as claimed in claim 1,
said receptacle being knitted in connected loops of substantially uniform pattern and number per square inch throughout the receptacle, whereby the shrinker exhibits generally uniform compression against the residual limb.

17. The above knee shrinker as claimed in claim 1,
said receptacle being formed of a dyeable fabric material.

18. The above knee shrinker as claimed in claim 1,
said receptacle being formed of a latex-free material.

19. The above knee shrinker as claimed in claim 1,
said receptacle being formed of an anti-fraying material.

* * * * *